(12) United States Patent
Gresham

(10) Patent No.: US 8,357,123 B2
(45) Date of Patent: Jan. 22, 2013

(54) SURGICAL PORTAL WITH GEL AND FABRIC SEAL ASSEMBLY

(75) Inventor: Richard D. Gresham, Guilford, CT (US)

(73) Assignee: Covidien LP, Mansfield, MA (US)

( * ) Notice: Subject to any disclaimer, the term of this patent is extended or adjusted under 35 U.S.C. 154(b) by 418 days.

(21) Appl. No.: 12/174,765

(22) Filed: Jul. 17, 2008

(65) Prior Publication Data

US 2009/0076464 A1    Mar. 19, 2009

Related U.S. Application Data

(60) Provisional application No. 60/994,049, filed on Sep. 17, 2007.

(51) Int. Cl.
*A61M 5/178* (2006.01)

(52) U.S. Cl. .............................. 604/167.02; 604/164.02

(58) Field of Classification Search .................. 604/30, 604/164.01, 164.02, 167.01–167.04, 167.06, 604/256, 164.03–166.01; 606/108, 167, 606/185, 213
See application file for complete search history.

(56) References Cited

U.S. PATENT DOCUMENTS

| | | |
|---|---|---|
| 3,402,710 A | 9/1968 | Paleschuck |
| 4,447,237 A | 5/1984 | Frisch et al. |
| 4,475,548 A | 10/1984 | Muto |
| 4,519,908 A | 5/1985 | Woodruff |
| 4,610,665 A | 9/1986 | Matsumoto et al. |
| 5,015,228 A | 5/1991 | Columbus et al. |
| 5,041,095 A | 8/1991 | Littrell |
| 5,104,389 A | 4/1992 | Deem et al. |
| 5,127,626 A | 7/1992 | Hilal et al. |
| 5,180,376 A | 1/1993 | Fischell |
| 5,207,656 A | 5/1993 | Kranys |
| 5,330,497 A | 7/1994 | Freitas et al. |
| 5,338,313 A | 8/1994 | Mollenauer et al. |
| 5,342,315 A | 8/1994 | Rowe et al. |
| 5,360,417 A | 11/1994 | Gravener et al. |
| 5,389,080 A | 2/1995 | Yoon |
| 5,389,081 A | 2/1995 | Castro |
| 5,391,153 A | 2/1995 | Haber et al. |
| 5,407,434 A | 4/1995 | Gross |
| 5,429,609 A | 7/1995 | Yoon |
| 5,441,486 A | 8/1995 | Yoon |
| 5,460,616 A | 10/1995 | Weinstein et al. |
| 5,480,410 A | 1/1996 | Cuschieri et al. |
| 5,484,425 A | 1/1996 | Fischell et al. |
| 5,514,109 A | 5/1996 | Mollenauer et al. |
| 5,514,133 A | 5/1996 | Golub et al. |
| 5,542,931 A | 8/1996 | Gravener et al. |
| 5,550,363 A | 8/1996 | Obata |

(Continued)

FOREIGN PATENT DOCUMENTS

AU    2005202133 A1    12/2006
(Continued)

OTHER PUBLICATIONS

European Search Report for corresponding EP 08252974 date of mailing is Feb. 6, 2009 (3 pages).

(Continued)

*Primary Examiner* — Kevin C Sirmons
*Assistant Examiner* — Kami A Bosworth

(57) ABSTRACT

A surgical portal assembly provides access to underlying tissue. The surgical portal has a seal which includes a gel layer and a fabric layer. The seal includes internal surfaces defining a passage for reception and passage of a surgical object in substantial sealed relation therewith.

16 Claims, 7 Drawing Sheets

U.S. PATENT DOCUMENTS

| | | | |
|---|---|---|---|
| 5,556,387 | A | 9/1996 | Mollenauer et al. |
| 5,603,702 | A | 2/1997 | Smith et al. |
| 5,628,732 | A | 5/1997 | Antoon, Jr. et al. |
| 5,634,908 | A | 6/1997 | Loomas |
| 5,634,937 | A | 6/1997 | Mollenauer et al. |
| 5,653,705 | A | 8/1997 | de la Torre et al. |
| 5,662,615 | A | 9/1997 | Blake, III |
| 5,722,958 | A | 3/1998 | Gravener et al. |
| 5,738,664 | A | 4/1998 | Erskine et al. |
| 5,741,298 | A | 4/1998 | MacLeod |
| 5,743,884 | A | 4/1998 | Hasson et al. |
| 5,779,697 | A | 7/1998 | Glowa et al. |
| 5,788,676 | A | 8/1998 | Yoon |
| 5,843,031 | A | 12/1998 | Hermann |
| 5,906,577 | A | 5/1999 | Beane et al. |
| 5,957,913 | A | 9/1999 | de la Torre et al. |
| 5,989,233 | A | 11/1999 | Yoon |
| 6,017,356 | A | 1/2000 | Frederick et al. |
| 6,024,736 | A | 2/2000 | de la Torre |
| 6,079,692 | A | 6/2000 | Powell |
| 6,110,154 | A | 8/2000 | Shimomura et al. |
| 6,315,770 | B1 | 11/2001 | de la Torre et al. |
| 6,319,246 | B1 | 11/2001 | de la Torre et al. |
| 6,355,014 | B1 | 3/2002 | Zadno-Azizi et al. |
| 6,440,063 | B1 | 8/2002 | Beane et al. |
| 6,482,181 | B1 | 11/2002 | Racenet et al. |
| 6,551,283 | B1 | 4/2003 | Guo et al. |
| 6,569,120 | B1 | 5/2003 | Green et al. |
| 6,602,240 | B2 | 8/2003 | Hermann et al. |
| 6,610,031 | B1 | 8/2003 | Chin |
| 6,663,598 | B1 | 12/2003 | Carrillo, Jr. et al. |
| 6,702,787 | B2 | 3/2004 | Racenet et al. |
| 6,712,791 | B2 | 3/2004 | Lui et al. |
| 7,052,454 | B2 | 5/2006 | Taylor |
| 7,153,261 | B2 | 12/2006 | Wenchell |
| 7,163,510 | B2 | 1/2007 | Kahle et al. |
| 7,235,062 | B2 | 6/2007 | Brustad |
| 7,244,244 | B2 | 7/2007 | Racenet et al. |
| 7,390,317 | B2 | 6/2008 | Taylor et al. |
| 7,473,221 | B2 | 1/2009 | Ewers et al. |
| 7,481,765 | B2 | 1/2009 | Ewers et al. |
| 2001/0041871 | A1 | 11/2001 | Brimhall |
| 2001/0049499 | A1 | 12/2001 | Lui et al. |
| 2001/0049508 | A1 | 12/2001 | Fangrow, Jr. et al. |
| 2002/0013552 | A1 | 1/2002 | Dennis |
| 2003/0032858 | A1 | 2/2003 | Ginn et al. |
| 2003/0040711 | A1 | 2/2003 | Racenet et al. |
| 2003/0050604 | A1 | 3/2003 | Lui et al. |
| 2003/0139756 | A1 | 7/2003 | Brustad |
| 2003/0195472 | A1 | 10/2003 | Green et al. |
| 2003/0208104 | A1 | 11/2003 | Carrillo, Jr. et al. |
| 2004/0015185 | A1 | 1/2004 | Ewers et al. |
| 2004/0054353 | A1 | 3/2004 | Taylor |
| 2004/0059297 | A1 | 3/2004 | Racenet et al. |
| 2004/0066008 | A1 | 4/2004 | Smith |
| 2004/0093018 | A1 | 5/2004 | Johnson |
| 2004/0106942 | A1 | 6/2004 | Taylor et al. |
| 2004/0111060 | A1 | 6/2004 | Racenet et al. |
| 2004/0254426 | A1 | 12/2004 | Wenchell |
| 2005/0020884 | A1 | 1/2005 | Hart et al. |
| 2005/0059934 | A1 | 3/2005 | Wenchell |
| 2005/0096605 | A1 | 5/2005 | Green et al. |
| 2005/0096695 | A1 | 5/2005 | Olich |
| 2005/0148823 | A1 | 7/2005 | Vaugh et al. |
| 2005/0165433 | A1 | 7/2005 | Haberland et al. |
| 2005/0212221 | A1 | 9/2005 | Smith et al. |
| 2005/0267419 | A1 | 12/2005 | Smith |
| 2006/0041232 | A1 | 2/2006 | Stearns et al. |
| 2006/0047284 | A1 | 3/2006 | Gresham |
| 2006/0047293 | A1 | 3/2006 | Haberland et al. |
| 2006/0084842 | A1 | 4/2006 | Hart et al. |
| 2006/0129165 | A1 | 6/2006 | Edoga et al. |
| 2006/0149305 | A1 | 7/2006 | Cuevas et al. |
| 2006/0224120 | A1 | 10/2006 | Smith et al. |
| 2006/0264991 | A1 | 11/2006 | Johnson et al. |
| 2006/0276751 | A1 | 12/2006 | Haberland et al. |
| 2007/0055107 | A1 | 3/2007 | Wenchell |
| 2007/0088241 | A1 | 4/2007 | Brustad et al. |
| 2007/0116854 | A1 | 5/2007 | Taylor et al. |
| 2007/0151566 | A1 | 7/2007 | Kahle et al. |
| 2007/0197972 | A1 | 8/2007 | Racenet et al. |
| 2007/0233006 | A1 | 10/2007 | Brustad |
| 2008/0011307 | A1 | 1/2008 | Beckman et al. |
| 2008/0033363 | A1 | 2/2008 | Haberland et al. |
| 2008/0077169 | A1 | 3/2008 | Taylor et al. |
| 2008/0086074 | A1 | 4/2008 | Taylor et al. |
| 2009/0048683 | A1 | 2/2009 | Morris et al. |

FOREIGN PATENT DOCUMENTS

| | | |
|---|---|---|
| DE | 3217118 | 8/1983 |
| DE | 3737121 | 11/1989 |
| EP | 0051718 | 5/1982 |
| EP | 0113520 | 7/1984 |
| EP | 0169787 | 1/1986 |
| EP | 0312219 | 4/1989 |
| EP | 0538060 | 4/1993 |
| EP | 1629787 | 3/2006 |
| EP | 1 698 291 | 6/2006 |
| GB | 1482857 | 8/1977 |
| JP | 50-112652 | 9/1975 |
| JP | 58163867 | 9/1983 |
| JP | 51-03854 | 4/1993 |
| JP | 06061518 | 4/1994 |
| JP | 07241298 | 9/1995 |
| WO | 93/04717 | 3/1993 |
| WO | 94/17844 | 8/1994 |
| WO | 95/13313 | 5/1995 |
| WO | 98/53865 | 3/1998 |
| WO | 02/087682 | 11/2002 |
| WO | 02087682 | 11/2002 |
| WO | 03011154 | 2/2003 |
| WO | 2004043275 | 5/2004 |
| WO | WO2007/119232 A | 10/2007 |

OTHER PUBLICATIONS

European Search Report, Application No. EP 08253234, dated Jan. 30, 2009.

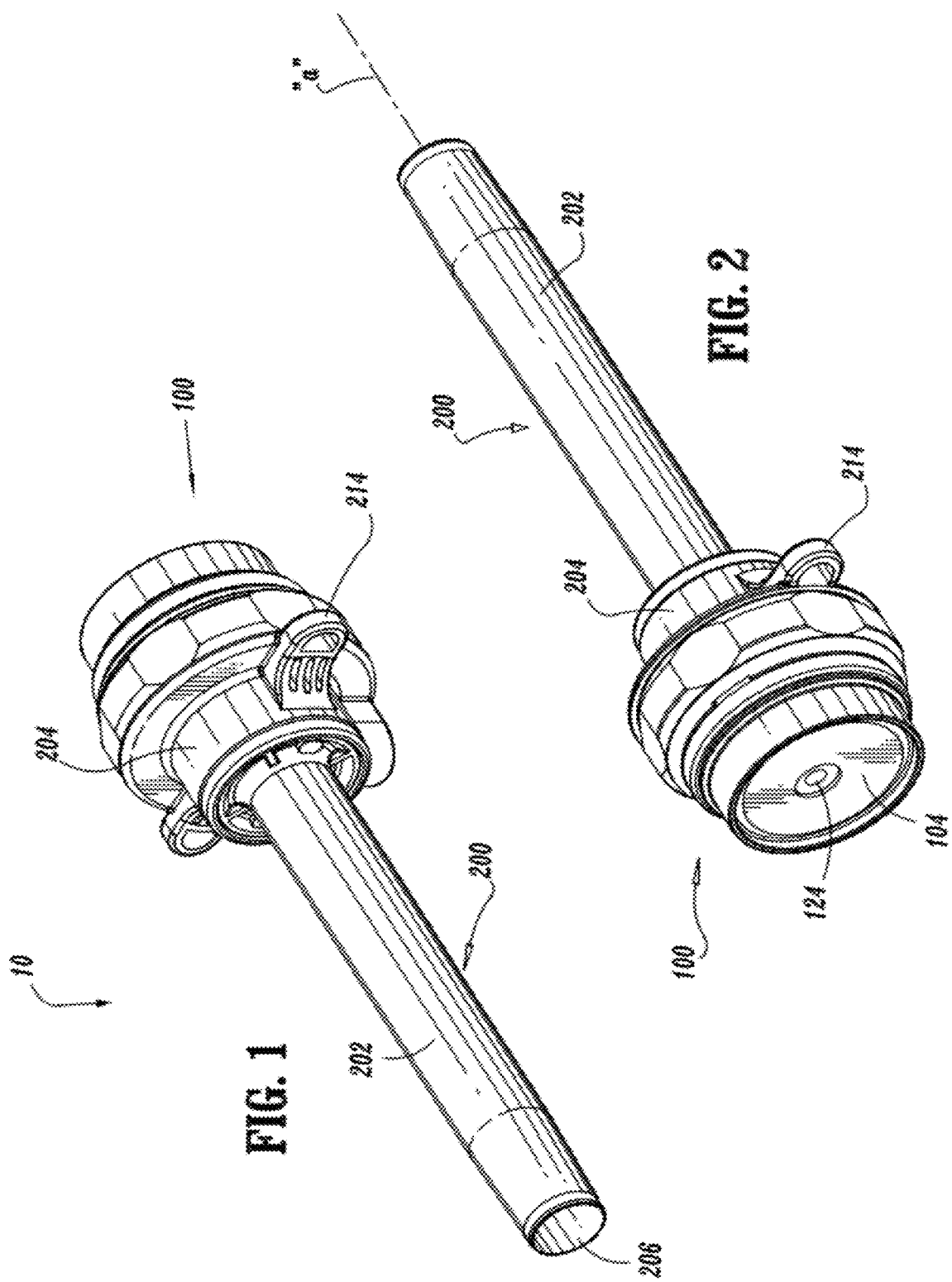

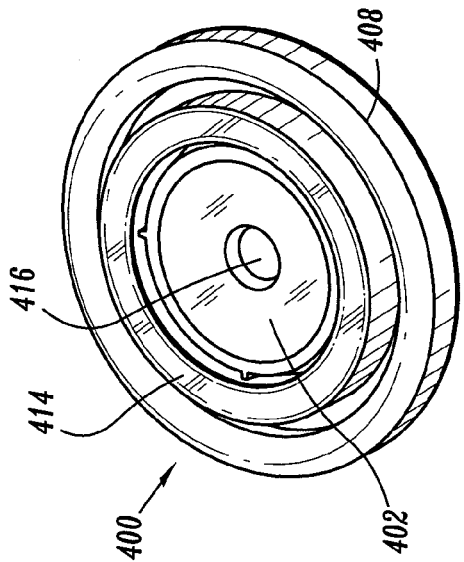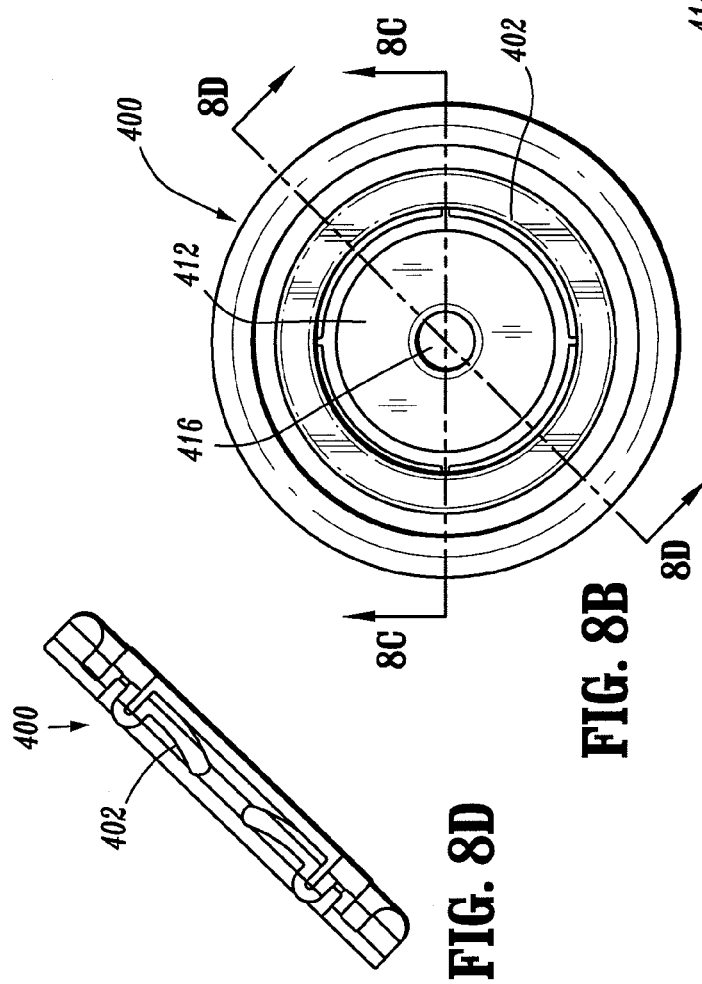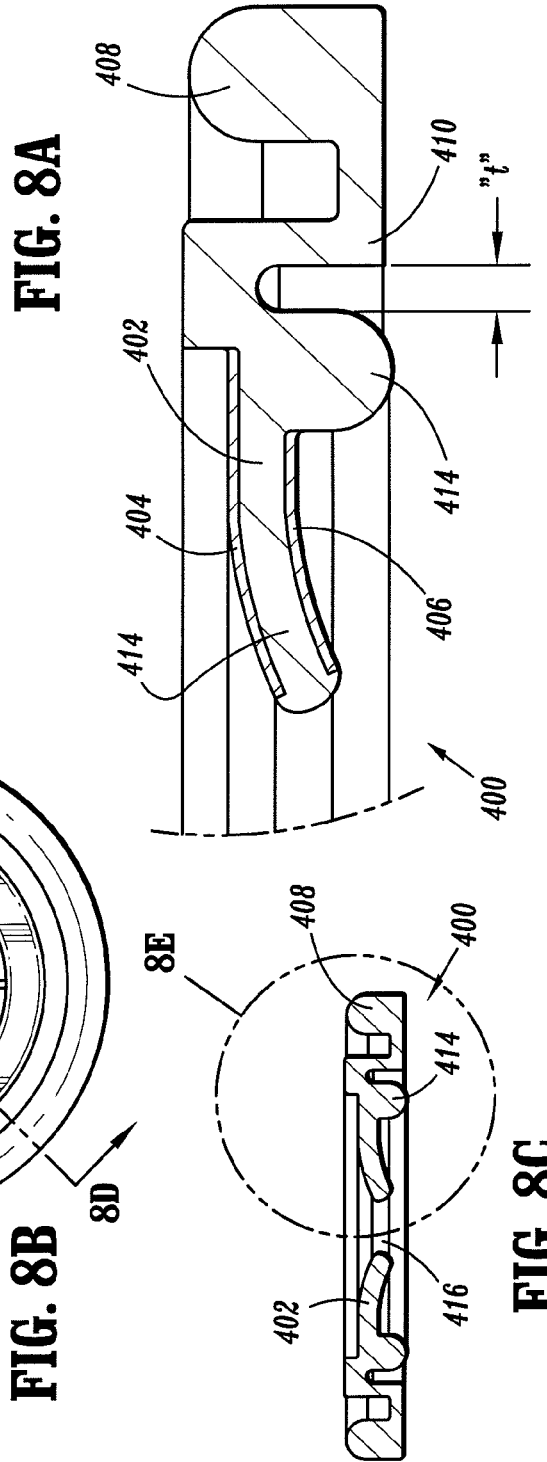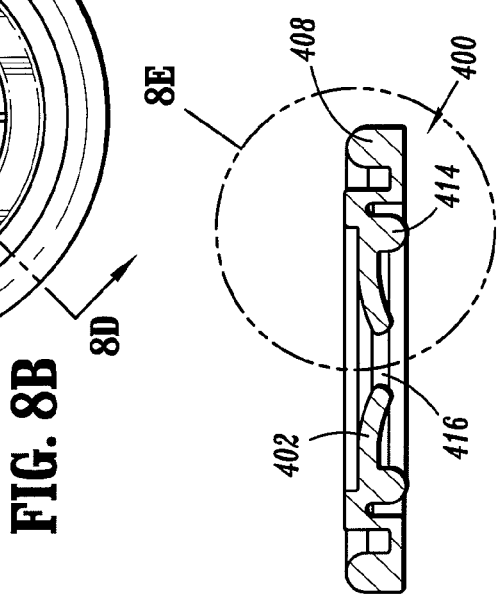

SURGICAL PORTAL WITH GEL AND FABRIC SEAL ASSEMBLY

CROSS REFERENCE TO RELATED APPLICATION

The present application claims the benefit of and priority to U.S. Provisional Application Ser. No. 60/994,049 filed on Sep. 17, 2007, the entire contents of which are incorporated herein by reference.

BACKGROUND

1. Field of the Disclosure

The present disclosure relates to surgical devices and, more particularly, to a seal assembly for use with a surgical portal apparatus during a minimally invasive surgical procedure.

2. Description of the Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

SUMMARY

The present disclosure is directed to further improvements in seal assemblies for use with portal apparatii during a surgical procedure. In accordance with one embodiment, a surgical portal assembly includes a portal adapted to provide access to underlying tissue and having a longitudinal opening extending along a longitudinal axis of the portal, and defining proximal and distal ends and a seal. The seal comprises a gel material and a fabric material mounted relative to the gel material. The seal includes internal surfaces defining a passage for reception and passage of a surgical object in substantial sealed relation therewith. A fabric layer may be mounted adjacent each of proximal and distal surfaces of the seal. The internal surfaces defining the passage of the seal may include the gel material whereby the gel material establishes the sealed relation with the surgical object. The seal includes an inner seal segment which may generally taper in a distal direction to define a general funnel configuration. Alternatively, the seal includes an inner seal segment which defines a general sloped portion to facilitate insertion of the surgical object and possibly minimize potential of inversion of the inner seal area upon withdrawal of the surgical object. The seal may include at least one support collar mounted adjacent a periphery of the seal element. The seal may further include an elastomeric material having a rigidity greater than the rigidity of the gel material.

BRIEF DESCRIPTION OF THE DRAWINGS

Preferred embodiments of the present disclosure will be better appreciated by reference to the drawings wherein:

FIGS. 1-2 are perspective views of a portal system in the form of a cannula assembly and a seal assembly in accordance with the principles of the present disclosure;

FIGS. 8A and 8B are respective perspective and plan views of another embodiment of the seal member;

FIGS. 8C and 8D are cross-sectional views of the seal member of FIGS. 8A and 8B taken along respective lines 8C-8C and 8D-8D of FIG. 8B;

FIG. 8E is an enlarged view of the area of detail identified in FIG. 8C; and

DETAILED DESCRIPTION

Figure 3:
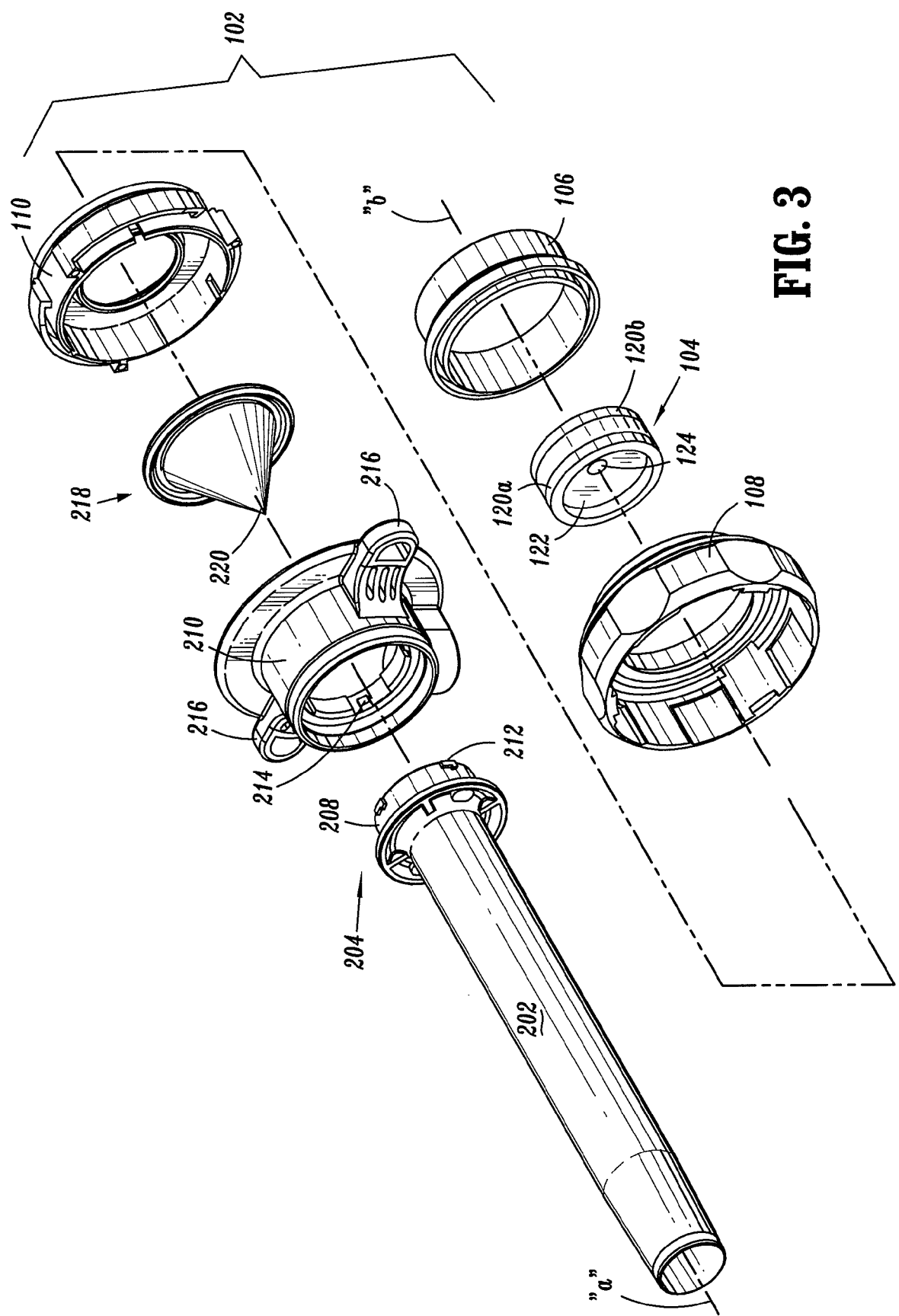
FIG. 3 is a perspective view with parts separated of the cannula and seal assemblies.

The portal system of the present disclosure incorporates a seal assembly which, either alone or in combination with a seal internal to a cannula assembly, provides a substantial seal between a body cavity of a patient and the outside atmosphere before, during and after insertion of an object through the cannula assembly. Moreover, the seal assembly is capable of accommodating objects of varying diameters, e.g., instruments from about 4.5 mm to about 15 mm, by providing a gas tight seal with each instrument when inserted. The flexibility of the seal assembly greatly facilitates endoscopic surgery where a variety of instruments having differing diameters are often needed during a single surgical procedure.

The seal assembly contemplates the introduction and manipulation of various types of instrumentation adapted for insertion through a trocar and/or cannula assembly while maintaining a fluid tight interface about the instrumentation to prevent gas and/or fluid leakage from the established pneumoperitoneum so as to preserve the atmospheric integrity of a surgical procedure. Specifically, the seal assembly accommodates angular manipulation of the surgical instrument relative to the seal axis. This feature of the seal assembly desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

The seal assembly may be a component of a portal system adapted to provide access to an underlying site. The seal assembly may be readily incorporated into a portal, such as a conventional trocar device or cannula, and provides the device with sealing capability about an inserted instrument.

The seal assembly may also be adapted to receive and form a seal about a physician's arm or hand during a hand-assisted laparoscopic procedure. In this application, the seal assembly is a component of an access member which is introduced within the body to provide access to underlying tissue in, e.g., the abdominal cavity.

Referring now to the drawings, in which like reference numerals identify identical or substantially similar parts throughout the several views, FIGS. 1-2 illustrate a portal system 10 of the present disclosure incorporating a seal assembly 100 mounted to an access device such as cannula assembly 200. Cannula assembly 200 may be any portal member suitable for the intended purpose of accessing a body cavity and typically defines a passageway permitting introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which may be blunt, a non-bladed, or a sharp pointed instrument positionable within the passageway of the cannula assembly 200. The obturator assembly is utilized to penetrate the abdominal wall or introduce the cannula assembly 200 through the abdominal wall, and then subsequently is removed from the cannula assembly 200 to permit introduction of the surgical instrumentation utilized to perform the procedure through the passageway.

Cannula assembly 200 includes cannula sleeve 202 and cannula housing 204 mounted to a proximal end of the cannula sleeve 202. Cannula sleeve 202 defines a longitudinal axis "a" extending along the length of the cannula sleeve 202. Cannula sleeve 202 further defines an internal longitudinal passage 206 dimensioned to permit passage of surgical instrumentation. Cannula sleeve 202 may be formed of any suitable medical grade material, such as stainless steel or other rigid materials, including polymeric materials, such as polycarbonate, or the like. Cannula sleeve 202 may be transparent or opaque. The diameter of cannula sleeve 202 may vary, but typically ranges from about 4.5 to about 15 mm.

Figure 4:
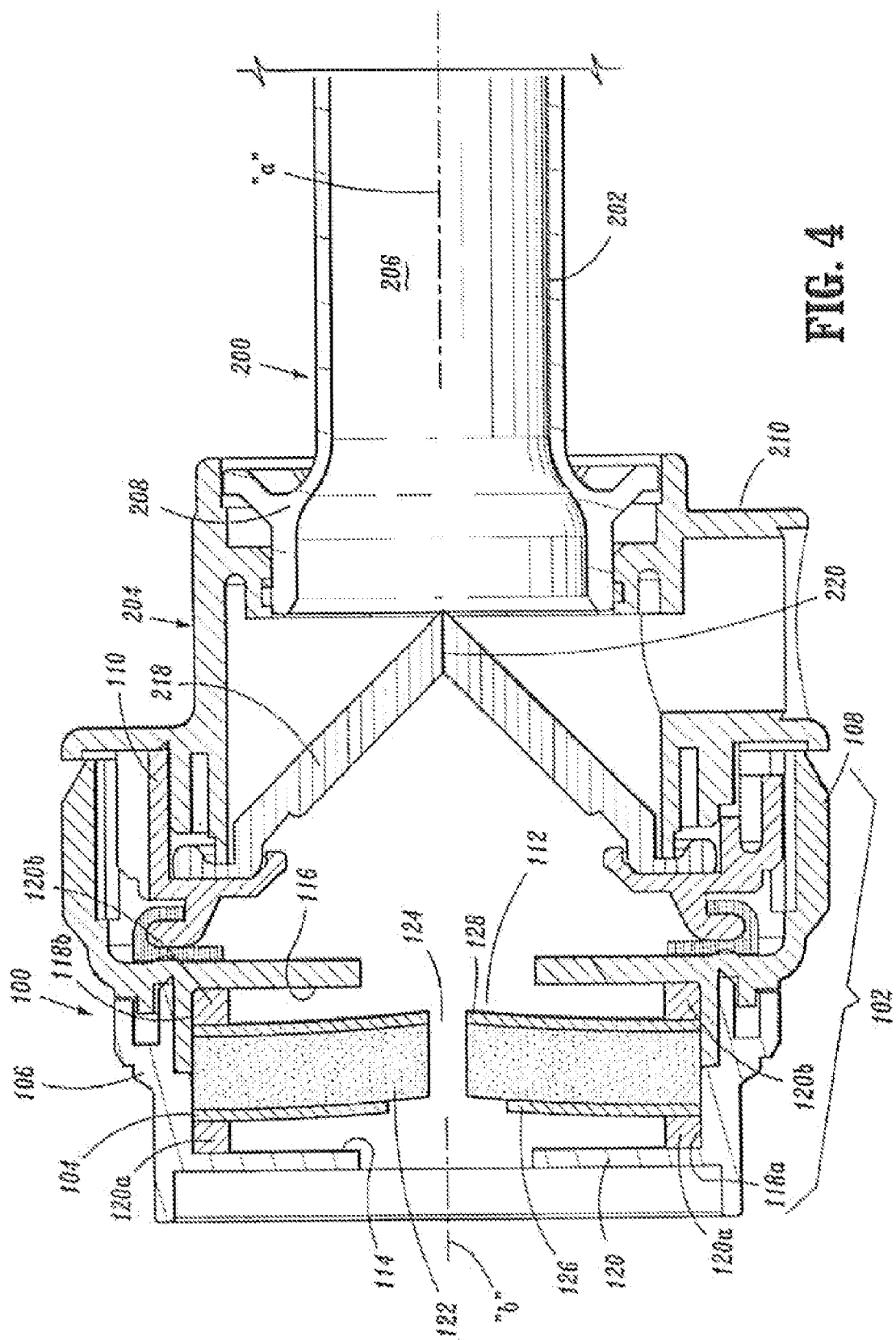
FIG. 4 is a side cross-sectional view of the cannula and seal assemblies.

Cannula housing 204 includes two components, specifically, housing flange 208 which is attached to the proximal end of cannula sleeve 202 and main housing 210 as shown in FIGS. 3-4. Main housing 210 is connectable to housing flange 208 through a bayonet coupling consisting of radially spaced tongues 212 on the exterior of housing flange 208 and corresponding recesses 214 within the interior of main housing 210, which are arranged to receive the tongues 212. Thereafter, housing flange 208 and main housing 210 are rotated to securely lock the tongues 212 within the recesses 214. Other conventional means, e.g., a threaded connection, snap fit, ultrasonic welding or any other means envisioned by one skilled in the art including, e.g., adhesive means, may be utilized to connect housing flange 208 and main housing 210. Main housing 210 further includes diametrically opposed housing grips 216 dimensioned and arranged for gripping engagement by the fingers of the user. Additionally or alternatively, suture anchors may extend from main housing 210. Although shown and described as two components, cannula housing 204 may be a single component and attached to cannula sleeve 202 by any of the aforementioned means. The housing flange 208, or the housing flange 208 and main housing 210, may be integrally formed with cannula sleeve 202.

With reference to FIG. 3, in conjunction with FIGS. 1-2, cannula housing 204 further includes valve 218. Valve 218 may be a zero-closure valve such as duck-bill valve having a slit 220 which is adapted to close in the absence of a surgical object and/or in response to insufflation gases of the pressurized cavity. In the alternative, valve 218 may be a gel seal, balloon valve, or a flapper valve.

Referring now to FIGS. 3-4, in conjunction with FIGS. 1-2, seal assembly 100 will be discussed in detail. Seal assembly 100 includes seal housing, generally identified as reference numeral 102, and seal 104 which is disposed within the seal housing 102. Seal housing 102 houses the sealing components of the assembly and defines the outer valve or seal body of the seal assembly 100. Seal housing 102 defines central seal housing axis "b" which is preferably parallel to the axis "a" of cannula sleeve 202 and, more specifically, coincident with the axis "a" of the cannula. Seal housing 102 incorporates three housing components, namely, first, second and third housing components 106, 108, 110, respectively, which, when assembled together, form the seal housing 102. Assembly of housing components 106, 108, 110 may be effected by any of the aforementioned connection means discussed with respect to cannula housing 204. Although shown and described as three components, it is appreciated that seal housing 102 may be a single component having the seal 104 mounted therein. In the assembled condition of housing components 106, 108, 110, an internal channel 112 is defined between upper and lower walls 114,116 and side walls 118a, 118b. Internal channel 112 houses seal 104.

With particular reference to FIGS. 3-4, seal 104 will be discussed in detail. Seal 104 includes proximal and distal annular support collars 120a, 120b and seal element 122 which is mounted within, or attached to, the support collars 120a, 120b. Support collars 120a, 120b and seal element 122 define a height preferably slightly less than the height of internal chamber 112 to form a close tolerance with the upper and lower walls 114,116 defining the internal chamber 112. Support collars 120a, 120b may be adapted to reciprocally slide within internal chamber 112 in general transverse relation to axis "b" thereby possibly permitting lateral movement of seal 104 within the internal chamber 122. Alternatively, support collars 120a, 120b, and, thus, seal 104, may be secured within internal chamber 112. Any means for supporting support collars 120a, 120b within internal chamber 122 are envisioned including cements, screws, pins, etc. Support collar 120 may comprise a plastic, metallic or elastomer material and may be monolithically formed with seal element 122.

Seal element 122 is a septum seal including an inner area defining central aperture 124 for sealed reception of a surgical instrument. Alternatively, aperture 124 may be in the form of any passage, slit or the like. Seal element 122 may comprise a gel composition or very-soft thermoplastic elastomer. Gels and soft thermoplastic materials contemplated for use are known under the trade names VERSAFLEX, FLEXPLAST, DYANFLEX and MONOPRENE. Other suitable materials include soft silicone and polyurethane composites. These materials may be adapted to be sufficiently compliant to absorb off axis motion of the instrument and may be semi-rigid gel or possess the ability to flow. Moreover, the compliant characteristics of seal element 122 may substantially minimize the formation of a gap around the instrument during off-set manipulation of the instrument. The presence of a gap would otherwise permit the undesired release of gases from the underlying pneumoperitioneum.

Seal element 122 also includes a fabric material or layer 126, 128 on each of the proximal and distal surfaces of seal element 122. A suitable fabric material includes a SPANDEX material containing 20% LYCRA commercially available from Milliken, and may be a layer or be stitched within seal element 122. The fabric may comprise a woven, knitted, braided, or non-woven material of polymeric materials. Other fabric materials are also envisioned. Fabric layers 126, 128 may be compression molded within the gel material during manufacture of seal member 104 or attached to the surfaces of seal element via adhesives, cements, or the like. The methodologies for attaching fabric layers 126, 128 to seal element 122 as disclosed in certain embodiments of the U.S. Pat. No. 6,702,787 to Racenet may be utilized. The entire disclosure of U.S. Pat. No. 6,702,787 to Racenet is hereby incorporated by reference herein. In one embodiment, collars 120a, 120b serve to encapsulate or sandwich fabric layers 126, 128 and seal element 122 adjacent respective peripheral areas of the components. As indicated hereinabove, the components may be mounted to each other via cements, adhesives, compression molding or the like. Another method for fabricating seal 104 is disclosed in commonly assigned U.S. provisional application Ser. No. 60/994,048 entitled COMPOSITE SEAL AND METHOD FOR MANUFACTURING filed under Express Mail Certificate No. EM075410432US on Sep. 17, 2007, (203-5439), the entire contents of which are hereby incorporated by reference herein.

In one embodiment, fabric layer 126 on proximal surface of seal element 122 extends from support collar 120a to a position spaced from central aperture 124. With this arrangement, the gel material circumscribing central aperture 124 is devoid of fabric material. This ensures that the gel material of seal element 122 engages the surgical instrument during introduction and passage of the surgical instrument through central aperture 124. Fabric layer 128 on trailing or distal surface of seal element 122 may extend from collar 120b to be coterminous with central aperture 124. In the alternative, fabric layer 128 may terminate at a location spaced from central aperture 124.

Fabric layers 126, 128 enhance the structural integrity of seal 104 by providing a support lattice or structure to encapsulate gel material of seal element 122. Fabric layers 126, 128 also may be protective elements preserving the gel material of seal element 122 from contact with the instrument during insertion and possibly withdrawal of the instrument through central aperture 124.

Figure 5:
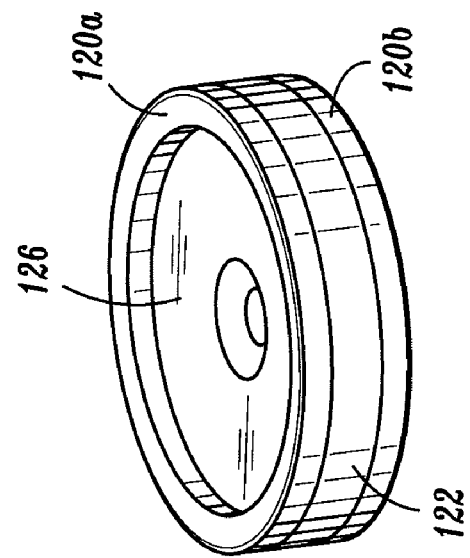
FIG. 5 is a perspective view of the seal member of the seal assembly.
Figure 6:
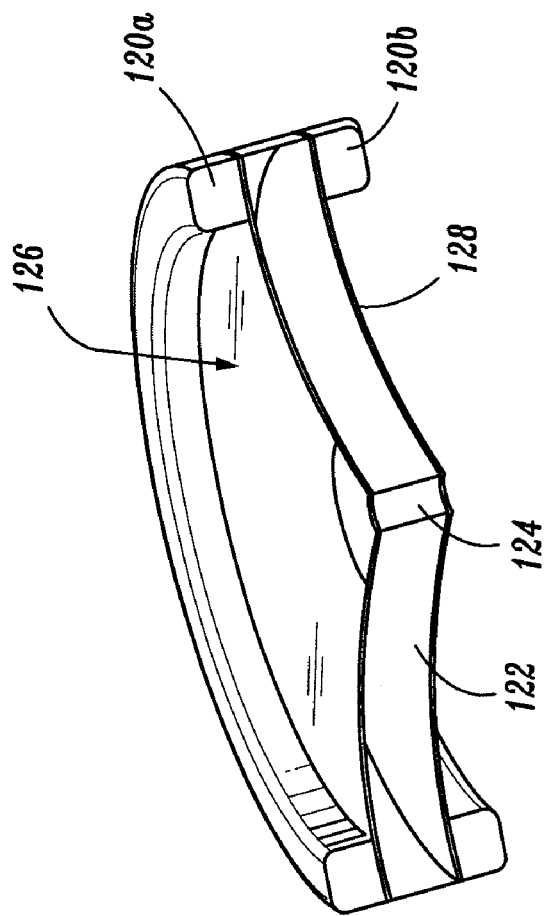
FIG. 6 is a perspective view with portions cut-away illustrating the seal member of the seal assembly.

As best depicted in FIGS. 5-6, seal element 122 may define a generally tapered or funneled profile whereby the seal element 122 slopes at an oblique angle with respect to the seal axis "b". The funneled characteristic may assist in guiding the instrument toward central aperture 124 during initial introduction of the instrument. The funneled characteristic also may substantially minimize the potential of inversion of seal element 122 during withdrawal of the instrument.

Seal member 104 may incorporate a lubricant or a therapeutic or pharmacological agent. Suitable lubricants include a coating of hydrocyclosiloxane prepared by plasma polymerization process. Such a coating is disclosed in U.S. Pat. No. 5,463,010 to Hu et al., the entire contents of which is hereby incorporated by reference. Examples of therapeutic or pharmacological agents include antimicrobials, antibacterials, hemostatic, moisture-providing agents, such as saline, healing agents, lubricious agents, antiseptics, growth factors, and/or anti-inflammatory agents.

Seal assembly 100 may be associated with, or joined to, cannula assembly 200 in a variety of ways. In a preferred embodiment, seal housing 102 of seal assembly 100 and cannula housing 204 of cannula assembly 200 are adapted to detachably engage each other, e.g., through a bayonet lock, threaded attachment, latching attachment, or like mechanical means. In further embodiments, cannula housing 204 and valve 218 may be omitted and seal assembly 100 may be removably or permanently attached to flange 206. The seal assembly may be mounted to cannula assembly 100 before during or after application of the cannula assembly within the operative site. Alternatively, the seal assembly 100 may be built within cannula housing 204 as depicted in FIG. 5. As a further alternative, seal assembly 100 may be incorporated within a housing of a hand access device utilized in hand-assisted laparoscopic procedures.

The use of the seal assembly 100 and cannula assembly 200 in connection with introduction of a surgical instrument will be discussed. Seal assembly 100 is mounted to cannula assembly 200 and the cannula assembly 200 is introduced into an insufflated abdominal cavity typically utilizing a sharp or non-blade trocar obturator. An instrument may be inserted into seal assembly 100 through seal 104 whereby the portions defining the aperture 124 of seal element 122 stretch to accommodate the instrument in substantial sealed relation therewith. The instrument is distally passed through the valve 218 and into the body cavity to perform the desired procedure. During manipulation of the instrument, the gel material of seal element 122 may flow, move or disperse with the instrument thereby filling any potential gaps which may form on opposed sides of the instrument.

Figure 7A:
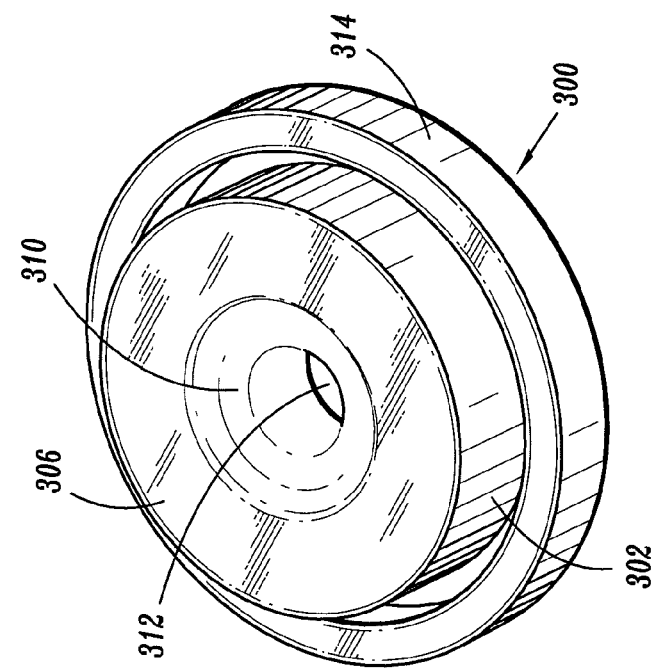
FIGS. 7A, 7B and 7C are respective perspective, plan and side-cross-sectional views of another embodiment of the seal member.
Figure 7B:
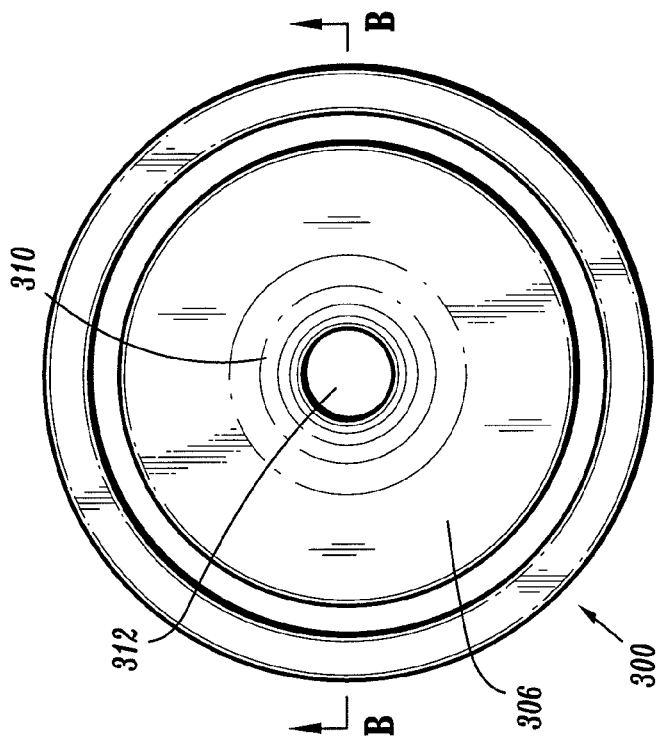
Figure 7C:
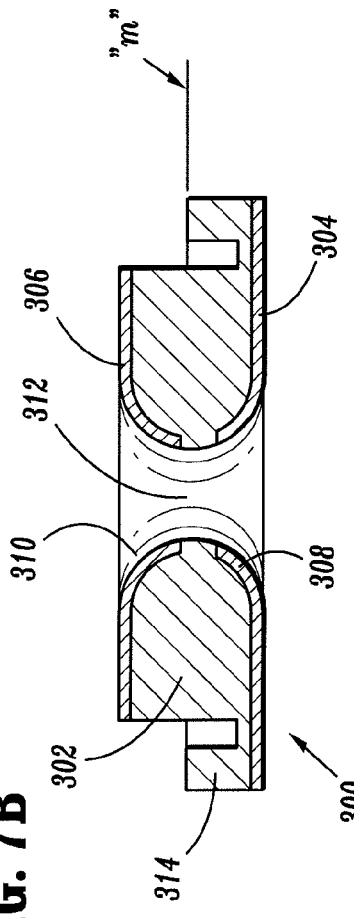

FIGS. 7A-7C illustrates another embodiment of the seal assembly 300 for use with cannula assembly 200. Seal assembly 300 includes seal element 302 and fabric layers 304, 306 connected to the trailing and leading surfaces of the seal element 302. Seal element 302 and fabric layers 304, 306 may comprise any of the materials identified hereinabove in connection with the embodiment of FIG. 1. Seal assembly 300 defines centrally located recesses 308, 310 on each of the trailing and leading surfaces of the seal assembly 300. Recesses 308, 310 define a slightly curved or parabolic profile extending towards median axis "m" of the seal assembly 300. This parabolic configuration may assist in insertion and withdrawal of the instrument through central seal aperture 312. In one embodiment, seal element 302 is devoid of fabric material adjacent central aperture 312 such that the gel material contacts the instrument in substantial sealed engagement therewith during insertion and withdrawal of the instrument. Fabric layers 304, 306 provide support for the gel material of seal element 302 and also may prevent direct engagement of the instrument with the gel material forming seal element 302. Seal assembly 300 also includes peripheral collar 314 which may be an extension of seal element 302, e.g., integrally molded with the seal element 302. Collar 314 may assist in securing seal assembly within cannula housing.

FIGS. 8A-8E illustrates another embodiment of the present disclosure. Seal assembly 400 includes seal element 402 and first and second fabric layers 404, 406 arranged in juxtaposed relation on opposed sides (e.g., proximal and distal) of the seal element 402. Seal element 402 and fabric layers 404, 406 may comprise any of the materials identified hereinabove with the earlier embodiments. Seal element 402 includes outer and inner annular collars 408, 410 and inner seal segment 412 depending at least radially inwardly from the inner collar 410. Outer and inner collars 408, 410 may assist in mounting seal element 402 within cannula housing 204. Inner seal segment 412 includes annular segment 414 depending from the distal surface of seal element 402. Annular segment 414 may be spaced from inner collar 410 a predetermined distance "t". This spacing or gap "t" may permit inner seal segment 412 to move in a transverse direction relative to seal axis "b" during introduction, manipulation and/or withdrawal of the instrument. Annular segment 414 may engage the internal lower wall 116 of seal housing 102 and outer and/or inner collar 408, 410 may contact either or both internal walls 116, 118 (FIG. 4) to assist in mounting seal assembly within seal housing.

Inner seal segment 412 may define a funnel appearance similar to the embodiment of seal element 102 of FIGS. 1-6. The funnel configuration may assist in directing the instrument toward seal aperture 416 and also minimize the potential of inversion of inner seal segment 412 during withdrawal of the instrument. The portion of inner seal segment 412 defining seal aperture 416 may be devoid of fabric whereby the gel material contacts the instrument. Alternatively, the fabric material may extend completely between fabric layers 404, 406.

Figure 9:
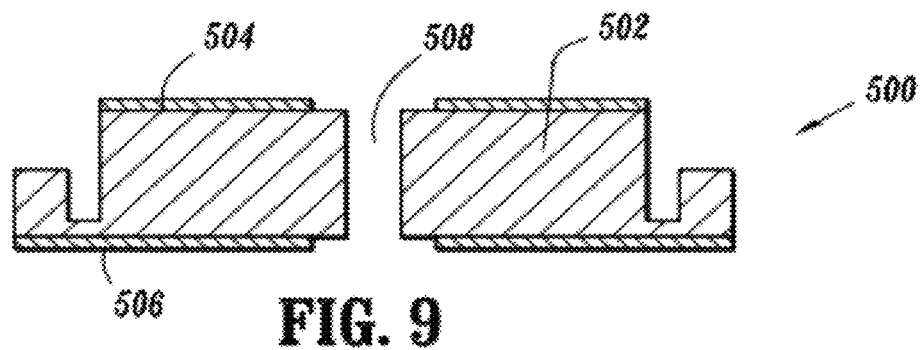
FIGS. 9-12 are side cross-sectional views of additional embodiments of the seal member of the seal assembly.

FIG. 9 illustrates an additional embodiment of the present disclosure. In FIG. 9 seal assembly 500 is generally a flat seal having seal element 502 and planar fabric layers 504, 506 on each side of the seal element. Seal element 502 defines central aperture 508. Fabric layers 504,506 extend radially inwardly to locations displaced from central aperture 508 such that gel material contacts instrument to form a seal about the instrument.

Figure 10:
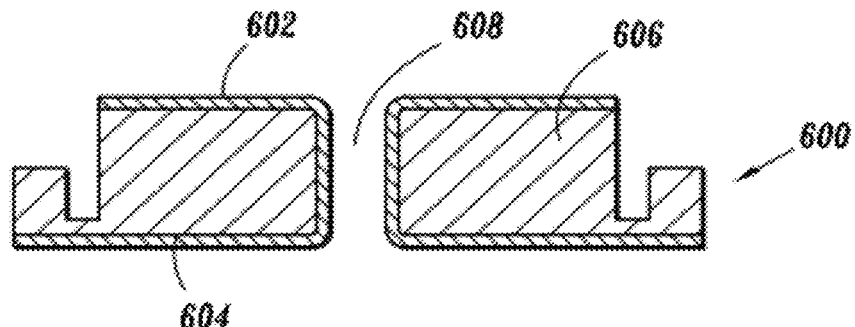

FIG. 10 illustrates an embodiment similar to the embodiment of FIG. 9; however, in accordance with this embodiment, seal assembly 600 incorporates fabric layers 602, 604 which extend continuously between the leading and trailing sides of seal element 606. Consequently, fabric material is adjacent central aperture 608. The fabric material of fabric layers 602, 604 may have an elastomer or gel embedded therein adjacent aperture 608 to enhance the sealing characteristics of seal assembly 600. In addition, a lubricious coating may be applied to the fabric adjacent central 608 aperture to ease passage of the instrument.

Figure 11:
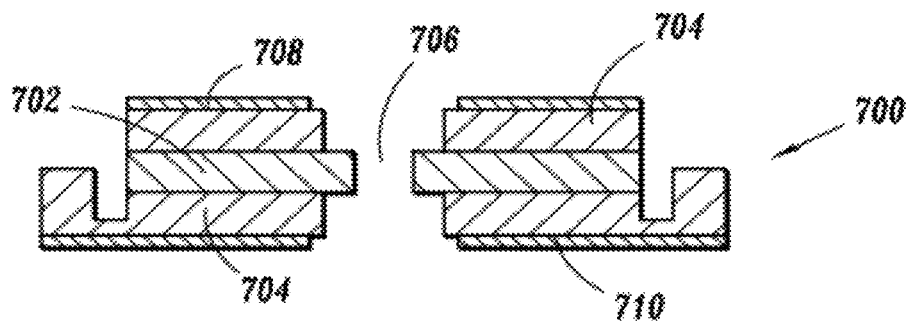

FIG. 11 illustrates another embodiment of the seal assembly of the present disclosure. Seal assembly 700 includes inner seal element 702 comprising a gel material and outer seal element 704 on each side of the inner seal element 702. Outer seal elements 704 each may include an elastomer having a greater degree of stiffness relative to the gel material of inner seal element 702. One suitable material for outer seal elements 704 is polyisoprene. The relatively rigid material of outer seal elements 704 may enhance the structural integrity of seal assembly 700 and also assist in forming a seal, e.g., around large size instruments. Inner seal element 702 extends radially inwardly to a greater degree than outer seal elements 704 to thereby define aperture or passageway 706. Alternatively, outer seal elements 704 may be coterminous with inner seal element 702. Fabric layers 708, 710 are mounted to each of outer seal elements 704.

Figure 12:
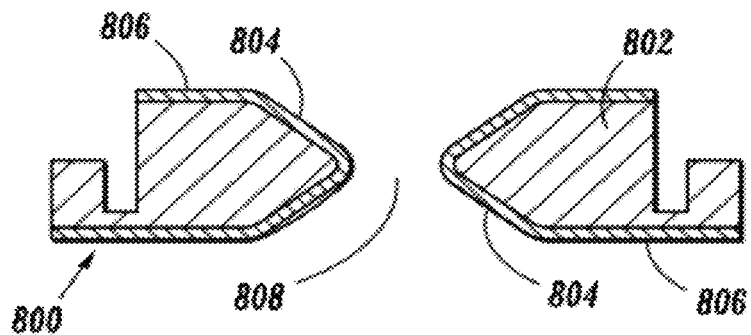

FIG. 12 illustrates another embodiment of the seal assembly. Seal assembly 800 includes seal element 802 having internal surfaces 804 which taper in a general linear manner toward median axis "m" from each side of seal element 802 thereby defining a generally triangular shape in cross-section of the inner area of the seal element 802. First and second fabric layers 806 are on each side of seal element 802 and may terminate at locations displaced from central aperture 808 such that the gel material of seal element 802 defines the central aperture 808.

The seal assembly of the present disclosure may include seals of various other shapes and constructions, such as a flat disc-shaped, conical, or hourglass-shaped member including a fabric material molded with a gel. The various configurations of the seals disclosed in certain embodiments of commonly assigned U.S. Pat. No. 6,702,787 to Racenet, the entire disclosure of which is hereby incorporated by reference, may be used in conjunction with a gel material as a seal element.

In a further alternative, the seal element may be arranged to have a constriction. For example, the seal element may have the general shape of an hourglass. The fabric can be a woven material, a braided material, or a knitted material. The type of material may be selected to provide a desired expansiveness. For example, a braid of varying en-count and angle may be selected. A preferred material is a synthetic material such as nylon, Kevlar (Trademark of E.I. DuPont de Nemours and Company) or any other material that will expand and compress about an instrument inserted therethrough. In addition, the fabric may be coated on its interior with urethane, silicon or other flexible lubricious materials to facilitate passage of an instrument or other object, such as the hand and arm, through the seal. In certain embodiments, the fabric is twisted about its axis so as to form a constriction or closed portion. The fabric is desirably constructed of a material and/or arranged so that the fabric forms a constriction or closure. The seal may also be molded so as to have a constriction or may be knitted, braided or woven so as to have a constriction.

It will be understood that various modifications and changes in form and detail may be made to the embodiments of the present disclosure without departing from the spirit and scope of the invention. Therefore, the above description should not be construed as limiting the invention but merely as exemplifications of preferred embodiments thereof. Those skilled in the art will envision other modifications within the scope and spirit of the present invention as defined by the claims appended hereto. Having thus described the invention with the details and particularity required by the patent laws, what is claimed and desired protected is set forth in the appended claims.

What is claimed is:

1. A surgical portal assembly, which comprises:
    a portal adapted to provide access to underlying tissue and having a longitudinal opening extending along a longitudinal axis of the portal, and defining proximal and distal ends; and
    a seal defining a median axis and a seal passage arranged about the median axis for reception and passage of a surgical object introduced through the portal, the seal including:
        a gel component having a gel material, and defining opposing proximal and distal faces; and
        first and second fabric components attached to respective proximal and distal faces of the gel component in superposed relation therewith and substantially encapsulating the gel component;
        the seal defining longitudinally opposed generally planar segments disposed radially outwardly with respect to the longitudinal axis and longitudinally opposed centrally located recesses disposed inwardly of the generally planar segments and leading into the seal passage with each recess arranged to define an outwardly curved and parabolic profile extending towards each other about the median axis of the seal and being coterminous with each other to assist in insertion and withdrawal of the surgical object through the seal passage.

2. A surgical portal assembly according to claim 1 wherein internal surfaces defining the seal passage include the gel component whereby the gel material establishes the sealed relation with the surgical object.

3. A surgical portal assembly according to claim 2 wherein the seal includes an inner seal segment, the inner seal segment generally tapering in a distal direction to define a general funnel configuration.

4. A surgical portal assembly according to claim 2 wherein the seal includes an inner seal segment, the inner seal segment defines a general sloped portion to facilitate insertion of the surgical object and minimize potential of inversion of the inner seal area upon withdrawal of the surgical object.

5. A surgical portal assembly according to claim 2 wherein the seal includes at least one support collar mounted adjacent a periphery of the seal element.

6. A surgical portal assembly according to claim 2 wherein the fabric components are dimensioned to encapsulate the gel component.

7. A surgical portal assembly according to claim 2 wherein the fabric components are each substantially planar fabric layers.

8. A surgical portal assembly according to claim 7 wherein the proximal and distal faces of the gel component are substantially orthogonal to the longitudinal axis of the portal.

9. A surgical portal assembly according to claim 2 wherein the internal surfaces defining the seal passage are devoid of the first and second fabric components whereby the gel material of the gel component establishes the sealed relation with the surgical object.

10. A surgical portal assembly according to claim 1, wherein the gel component of the seal defines a generally centrally located recess within at least one of the proximal and distal faces thereof, and adjacent the passage of the seal.

11. A surgical portal assembly according to claim 10 wherein the proximal and distal faces of the gel component of the seal include respective central portions which taper radially inward towards each other and relative to the median axis of the seal.

12. A surgical portal assembly according to claim 1 wherein the seal is a septum seal.

13. A surgical portal assembly according to claim 1 wherein the seal further includes an elastomeric material having a rigidity greater than a rigidity of the gel material of the gel component.

14. A surgical portal assembly, which comprises:
a portal adapted to provide access to underlying tissue and having a longitudinal opening extending along a longitudinal axis of the portal, and defining proximal and distal ends; and
a seal defining a seal passage for reception and passage of a surgical object introduced through the portal, the seal comprising:
a gel component having a gel material, and opposed proximal and distal face segments in general orthogonal relation to the longitudinal axis; and
first and second fabric layers attached to respective proximal and distal face segments of the gel component in a superposed relation therewith to substantially encapsulate a major portion of the gel component, the gel component defining centrally located recesses adjacent the respective proximal and distal face segments of the gel component and leading into the seal passage with each recess arranged to define an outwardly curved and parabolic profile extending towards each other about a median axis of the seal and being coterminous with each other to assist in insertion and withdrawal of the surgical object through the seal passage.

15. A surgical portal assembly according to claim 14 wherein the seal includes an outer segment and an inner segment, the inner segment having opposed recessed inner surfaces defining the seal passage, the inner recessed surfaces generally tapering radially inwardly relative to the longitudinal axis and towards each other to define a reduced thickness of the inner segment relative to the outer segment to facilitate passage of the surgical object.

16. A surgical portal assembly according to claim 15 wherein the gel component includes the inner segment whereby gel material defines the seal passage.

* * * * *